United States Patent

Mestre et al.

[11] Patent Number: 4,670,446
[45] Date of Patent: Jun. 2, 1987

[54] 1-(4-QUINOLYL)-2 OR 3-(4-PIPERIDYL)-ETHANAMINE AND -PROPANAMINE DERIVATIVES, AND THEIR USE

[75] Inventors: Michel Mestre, Paris; Christian Renault, Taverny, both of France

[73] Assignee: Rhone-Poulenc Sante, Courbevoie, France

[21] Appl. No.: 709,059

[22] Filed: Mar. 6, 1985

[30] Foreign Application Priority Data

Mar. 9, 1984 [FR] France ............... 84 03669

[51] Int. Cl.⁴ .................. C07D 401/06; A61K 31/445
[52] U.S. Cl. ..................................... 514/314; 546/176
[58] Field of Search .......................... 546/176; 514/314

[56] References Cited

FOREIGN PATENT DOCUMENTS 0035819 9/1981 European Pat. Off. ............ 546/176
0053964 6/1982 European Pat. Off. .

OTHER PUBLICATIONS

Morgan et al., J. of Pharm. Sci., 65, pp. 635–648 (1976).

Primary Examiner—Glennon H. Hollrah
Assistant Examiner—D. B. Springer
Attorney, Agent, or Firm—Stevens, Davis, Miller & Mosher

[57] ABSTRACT

The invention provides the compounds of formula

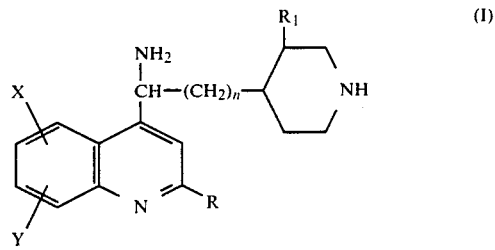

in which
n equals 1 or 2,
R denotes hydrogen, alkyl of 1 to 4 carbon atoms or phenyl,
$R_1$ denotes hydrogen, alkyl of 1 to 4 carbon atoms or alkenyl of 2 to 4 carbon atoms, X and Y, which may be identical or different, are each attached to the quinoline ring system in position 5, 6, 7 or 8, and each denote hydrogen or alkoxy of 1 to 3 carbon atoms. These compounds are useful in the treatment of cardiac arrhythmias.

7 Claims, No Drawings

1-(4-QUINOLYL)-2 OR 3-(4-PIPERIDYL)-ETHANAMINE AND -PROPANAMINE DERIVATIVES, AND THEIR USE

The present invention provides new 1-(4-quinolyl)-2-(4-piperidyl)ethanamine and 1-(4-quinolyl)-3-(4-piperidyl)-propanamine derivatives of the formula

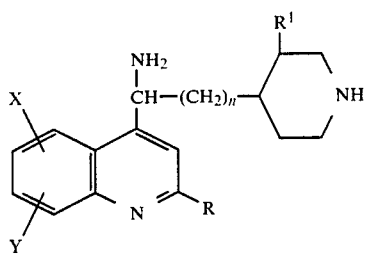

in which n equals 1 or 2, R denotes hydrogen, alkyl of 1 to 4 carbon atoms or phenyl, $R_1$ denotes hydrogen, alkyl of 1 to 4 carbon atoms or alkenyl of 2 to 4 carbon atoms, X and Y, which may be identical or different, are each attached to the quinoline ring system in position 5, 6, 7 or 8, and each denote hydrogen or alkoxy of 1 to 3 carbon atoms, in the form of their diastereoisomers, racemates, and enantiomers, and their acid salts. These compounds are useful in the treatment or prevention of cardiac arrhythmias.

The preferred compounds are those in which Y is hydrogen, X is hydrogen or methoxy, R is hydrogen, tert-butyl group or phenyl, and $R_1$ is hydrogen, ethenyl or ethyl.

When $R_1$ is hydrogen, the molecule of the compounds of formula (I) contains an asymmetric carbon atom (the carbon atom bearing the amino group) and hence, for a given significance of X, Y, R, $R_1$ and n, there are one racemate and two enantiomers.

When $R_1$ does not denote a hydrogen atom, the molecule of the compounds of formula (I) contains 3 assymmetric carbon atoms and hence, for a given significance of X, Y, R, $R_1$ and n, there are 8 stereoisomers, the respective formulae of which correspond to the 3-by-3 combinations of the rectus (R) or sinister (S) configurations of each asymmetric centre.

These various isomers form part of the invention, as do the acid addition salts of the compounds of formula (I) with inorganic or organic acids.

The compounds of formula (I) can be prepared from the ketones of formula

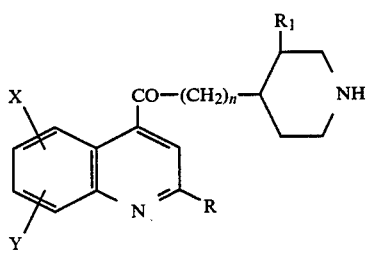

in which n, X, Y, R and $R_1$ are as hereinbefore defined, by processes for converting a ketone into a primary amine, such as those, for example, described in C. A. BUEHLER and D. E. PEARSON, Survey of Organic Synthesis, Wiley Interscience, vol. 1, 1970, p. 423 and 427.

An advantageous method consists in treating the ketone of formula (II) with ammonium formate, e.g. at a temperature from 150° to 200° C., and hydrolysing the product, e.g. in an acidic aqueous medium under reflux.

Another method consists in treating the ketone of formula (II) with hydroxylamine in a solvent such as ethanol at a temperature from room temperature to the boiling point of the solvent, and then reducing the oxime obtained, e.g. by a process described in HOUBEN-WEYL, Methoden der Organischen Chemie, 11, (1) p. 495 (Georg. Thieme Verlag—Stuttgart, 1957).

An especially advantageous method of reducing the oxime consists in using zinc powder in aqueous alcoholic ammoniacal medium.

When $R_1$ is a hydrogen atom, the ketones of formula (II) lead to racemic compounds of formula (I).

When $R_1$ is not a hydrogen atom, the ketones of formula (II) leads to a mixture of racemic or optically active diastereoisomeric compounds depending on whether the starting ketone is racemic or optically active.

The compounds of formula (I) in which $R_1$ denotes an alkyl group containing 2 to 4 carbon atoms can also be prepared by catalytic hydrogenation of the corresponding compounds of formula (I) in which $R_1$ denotes an alkenyl group having 2 to 4 carbon atoms. This hydrogenation can, for example, be carried out at room temperature under a hydrogen pressure equal to atmospheric pressure, in an inert solvent such as an alcohol, e.g. methanol or ethanol, in the presence of a catalyst such as palladium, nickel, rhodium, ruthenium or platinum.

The pure diastereoisomers can be isolated from the mixture by conventional methods such as chromatography, fractional crystallisation, salt formation and regeneration of base.

The ketones of formula (II) can be prepared by the process described in French Pat. No. 2,495,470.

The Examples which follow illustrate the invention.

EXAMPLE 1

3-[3(R)-ETHENYL-4(R)-PIPERIDYL]-1-(6-METHOXY-4-QUINOLYL)-1(RS)-PROPANAMINE

A mixture of quinicine (21 g), hydroxylamine hydrochloride (5.5 g) and anhydrous sodium acetate (6.4 g) in ethanol (260 ml) is boiled under reflux for 24 hours. The ethanol is evaporated, the residue taken up in water, the aqueous solution made alkaline with aqueous ammonia, and the insoluble material extracted with ethyl acetate.

The organic phase is washed with water, dried over anhydrous magnesium sulphate and evaporated to dryness under reduced pressure. A product (21 g) is obtained which is taken up in a mixture of ethanol (125 ml), water (125 ml) and concentrated aqueous ammonia (19 ml) to which ammonium acetate (5 g) is added. The mixture is stirred at room temperature and zinc powder (19 g) added in portions. The mixture is finally refluxed for 3 hours.

After cooling, the mixture is filtered through kieselguhr and ethanol removed under reduced pressure. The residue is taken up in water, the aqueous phase is made alkaline using sodium hydroxide, and the oil which separates out is extracted with chloroform. The organic phase is washed with water, dried and evaporated to dryness under reduced pressure. A product (20 g) is obtained which is chromatographed on silica gel using an ethanol/diethylamine (99:1) mixture as eluent. A product (16 g) is obtained which is treated with fumaric acid (2.81 g) in ethanol. After recrystallisation from the same solvent, 3-[3R-ethenyl-4(R)-piperidyl]-1-(6-methoxy-4-quinolyl)-1(RS)propanamine (5.2 g) is obtained as the sesquifumarate, m.p. 220° C.

EXAMPLE 2

1-[2-(1,1-DIMETHYLETHYL)-4-QUINOLYL]-3-(4-PIPERIDYL)-1-PROPANAMINE

To 1-[2-(1,1-dimethylethyl)-4-quinolyl]-3-(4-piperidyl)-1-propanone (6 g), ammonium formate (15 g) is added and the mixture is heated at 160° C. for 8 hours. After being cooled, the mixture is taken up in methylene chloride and water. The organic phase is washed with water, dried and evaporated to dryness under reduced pressure. The residue is taken up in 6N hydrochloric acid (60 ml) and the mixture is refluxed for 22 hours.

The mixture is then diluted with water. The solution is made alkaline with concentrated caustic soda solution and the insoluble material is extracted with methylene chloride. The organic phase is washed with water, dried over anhydrous magnesium sulphate and evaporated to dryness under reduced pressure. A product (4.1 g) is obtained which is converted into the di-hydrochloride in ethanol. After recrystallisation from 95% ethanol, 1-[2-(1,1-dimethylethyl)-4-quinolyl]-3-(4-piperidyl)-1-propanamine dihydrochloride (1.55 g) is obtained, m.p. above 265° C.

1-[2-(1,1-Dimethylethyl)-4-quinolyl]-3-(4-piperidyl)-1-propanone hydrochloride can be prepared as described in French Pat. No. 2,495,470.

EXAMPLE 3

1-(2-PHENYL-4-QUINOLYL)-2-(4-PIPERIDYL)ETHANAMINE

A mixture of 1-(2-phenyl-4-quinolyl)-2-(4-piperidyl)ethanone (11 g) and ammonium formate (27.3 g) is heated at 190° C. for 18 hours. After being cooled, the reaction medium is taken up in chloroform and water. The organic phase is washed with water, dried over magnesium sulphate and evaporated to dryness under reduced pressure. The residue is chromatographed on silica gel with a chloroform/diethylamine (9:1) mixture as eluent. After concentration of the requisite fractions, a product (11.6 g) is obtained which is taken up in 6N hydrochloric acid (70 ml) and boiled for 18 hours.

After being cooled, the aqueous phase is washed with ethyl ether and made alkaline with concentrated ammonia solution. The insoluble material is extracted with chloroform. The chloroform solution is washed with water, dried over magnesium sulphate and evaporated to dryness under reduced pressure. A product (8 g) is obtained which is chromatographed on silica gel with a chloroform/methanol/diethylamine (8:1:1) mixture as eluent. On concentration of the requisite fractions, a product (4 g) is obtained which is treated with ethanolic hydrogen chloride. 1-(2-Phenyl-4-quinolyl)-2-(4-piperidyl)ethanamine (1.1 g) is thus obtained as the dihydrochloride, m.p. 226° C.

1-(2-Phenyl-4-quinolyl)-2-(4-piperidyl)ethanone can be prepared as described in French Pat. No. 2,471,981.

EXAMPLE 4

3-[3(R)-ETHYL-4(R)-PIPERIDYL]-1-(6-METHOXY-4 QUINOLYL)-1(RS)-PROPANAMINE

3-[3(R)-ethenyl-4(R)-piperidyl]-1-(6-methoxy-4-quinolyl)-1(RS)-propanamine (1.2 g) dissolved in absolute ethanol (25 ml) is hydrogenated at atmospheric pressure and at room temperature in the presence of palladium (0.25 g, 10% on carbon). The absorption of hydrogen is complete in 2 hours. The catalyst is filtered off, the solvent is evaporated under reduced pressure, and the residue is recrystallised from isopropanol. 3-[3(R)-Ethyl-4(R)-piperidyl]-1-(6-methoxy-4 quinolyl)-1(RS)-propanamine is thus obtained as the trihydrochloride, m.p. 200° C.

The proton NMR spectrum of the base is deuterated chloroform has the following characteristics:

$CH_3O$—δ: 3.9 ppm, $H_2$ δ: 8.7 ppm, $H_3$ δ: 7.5 ppm, $H_5$ δ: 7.3 ppm, $H_8$ δ: 8.0 ppm.

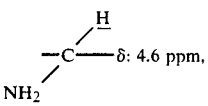

—$CH_2$—$\underline{CH_3}$ δ: 0.8 ppm.

The antiarrhythmic activity of the compounds of formula (I) has been demonstrated by means of the aconitine test.

The principle of the technique rests on the time taken by aconitine to induce ventricular arrhythmias when it is slowly perfused in rats. An antiarrhythmic substance delays the appearance of the arrhythmia and this delay is proportional to the activity of the substance.

Groups of 5 male rats are used. Individual anaesthetisation is carried out (10% urethane: 1 g/kg/ip) to permit catheterisation of the vein of the penis. The electrocardiogram is recorded. At time T=0, the substance being studied is injected as an aqueous solution, in the proportion of 2.5 ml of solution per kg, in the course of 30 seconds. At time T=60 seconds, i.e. 30 seconds after completing the injection, aconitine is perfused at the rate of 20 μg per minute until supraventricular extrasystoles appear. The perfusion time of the aconitine is noted.

The results are expressed as $ED_{50}$, i.e. the dose of the product under test in mg/kg which increases by 50% the perfusion time of aconitine relative to control animals.

The results obtained are collated in the Table below:

| Product of | $ED_{50}$ mg/kg i.v. |
|---|---|
| Example 1 | 5 |
| Example 2 | 1.2 |
| Example 3 | 0.38 |
| QUINDINE | 7.5 |

The compounds of formula (I) thus have exceptional antiarrhythmic properties and are more active than quinidine.

The acute toxicities of the compounds of the invention were determined by intravenous administration to male $CD_1$ mice (Charles RIVER). The $LD_{50}$ values were calculated after 3 days of observation by the cumulative method of J. J. REED and H. MUENCH (Amer. J. Hyg. 1938, 27, 493). The LD$_{50}$ values of the compounds of formula (I) are greater than 15 mg/kg i.v.

The compounds of formula I and their pharmaceutically acceptable acid addition salts can be used in human therapy for treating and/or preventing disturbances of cardiac rhythm. For this purpose they may be used in the form of pharmaceutical compositions comprising, as active ingredient, a compound of formula I, or a pharmaceutically acceptable acid addition salt thereof. In these compositions, the active ingredient may be in association with a compatible pharmaceutically acceptable diluent, adjuvant or coating which is usually a solid or semi-solid, a liquid containing a sweetener, flavouring, thickener, colorant, stabilizer, and/or wetting agent, or a sterile injectable liquid. Such compositions may normally contain 1 to 95% by weight of the active ingredient.

The compositions of the invention may be given by oral (including sub-lingual), parenteral, or rectal administration.

Solid compositions for oral administration may be tablets, pills, powders (particularly in gelatin capsules or cachets) or granules. In these compositions, the active compound of the invention may be mixed with one or more inert diluents such as starch, cellulose, sucrose, lactose or silica. These compositions may also contain substances other than diluents, for example one or more lubricants such as magnesium stearate or talc, a colorant, a coating (coated tablets) or a varnish.

Liquid compositions for oral administration may be solutions, suspensions, emulsions, syrups and pharmaceutically acceptable elixirs containing inert diluents such as water, ethanol, glycerol, vegetable oils or paraffin oils. These compositions may contain substances other than diluents, for example wetting agents, sweeteners, thickeners, flavourings, colorants or stabilisers.

Sterile compositions for parenteral administration are preferably aqueous or non-aqueous solutions, suspensions or emulsions. The solvent or vehicle may be, for example, water, propylene glycol, polyethylene glycol, a vegetable oil, especially olive oil, an injectable organic ester, for example ethyl oleate, or other suitable organic solvent. These compositions may also contain adjuvants, in particular wetting agents, isotonising agents, emulsifiers, dispersants and stabilisers. Sterilisation may be carried out in various ways, for example by asepticising filtration, by incorporating sterilising agents in the composition, by irradiation or by heating. The compositions may also be prepared in the form of sterile solid compositions which may be dissolved at the time of use in an injectable sterile medium.

The compositions for rectal administration may be suppositories or rectal capsules which, in addition to the active product, contain a semi-solid excipient such as cocoa butter, a semi-synthetic glyceride or a polyethylene glycol.

The dosage depends on the effect sought, the condition of the patient, and the administration route used. For example, for oral administration to an adult of, e.g. 70 kg., it can be between 50 and 800 mg of active substance per 24 hours, each unit dose containing from 10 to 100 mg of the active ingredient.

We claim:

1. A compound of formula

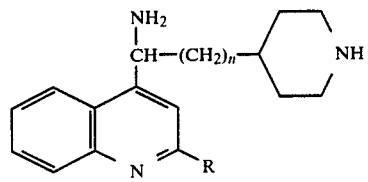

in which n is 1 or 2, and R denotes alkyl of 1 to 4 carbon atoms or phenyl, and its pharmaceutically acceptable acid addition salts.

2. A compound according to claim 1, in which R denotes tert-butyl or phenyl, and its pharmaceutically acceptable acid addition salts.

3. A compound according to claim 1 which is 1-[2-(1,1-dimethylethyl)-4-quinolyl]-3-(4-piperidyl)-1-propanamine and its pharmaceutically acceptable acid addition salts.

4. A compound according to claim 1 which is 1-(2-phenyl-4-quinolyl)-2-(4-piperidyl)ethanamine and its pharmaceutically acceptable acid addition salts.

5. A pharmaceutical composition comprising, as active ingredient, a compound as claimed in claim 1, or a pharmaceutically acceptable acid addition salt thereof.

6. A composition according to claim 5 in which the active ingredient is 1-(2-phenyl-4-quinolyl)-2-(4-piperidyl)-ethanamine.

7. Method of treating or preventing cardiac arrhythmia which comprises administering to a subject an effective amount of a compound as claimed in claim 1 or a pharmaceutically acceptable acid addition salt thereof.

* * * * *